(12) United States Patent
Manwaring et al.

(10) Patent No.: US 6,950,699 B1
(45) Date of Patent: Sep. 27, 2005

(54) WATER CONTENT PROBE

(75) Inventors: Kim Manwaring, Provo, UT (US);
Mark L. Manwaring, Pullman, WA (US)

(73) Assignee: Brain Child Foundation, Carefree, AZ (US)

( * ) Notice: Subject to any disclaimer, the term of this patent is extended or adjusted under 35 U.S.C. 154(b) by 756 days.

(21) Appl. No.: 10/017,820

(22) Filed: Dec. 12, 2001

(51) Int. Cl.⁷ ............................................... A61B 5/05
(52) U.S. Cl. ..................................................... 600/547
(58) Field of Search ................................ 600/554, 547; 606/32

(56) References Cited

U.S. PATENT DOCUMENTS

| | | | | |
|---|---|---|---|---|
| 4,488,559 A | * | 12/1984 | Iskander | ...................... 600/430 |
| 4,690,149 A | * | 9/1987 | Ko | .............................. 600/409 |
| 4,819,648 A | * | 4/1989 | Ko | .............................. 600/409 |
| 6,512,949 B1 | * | 1/2003 | Combs et al. | .............. 600/547 |

\* cited by examiner

Primary Examiner—Eric F. Winakur
Assistant Examiner—Matthew Kremer
(74) Attorney, Agent, or Firm—Mayer, Brown, Rowe & Maw LLP

(57) ABSTRACT

A method and system to determine brain stiffness is disclosed. A probe to measure tissue water content is inserted through an aperture (burr hole) in the cranium into brain tissue. The probe has two electrically separated plate conductors with a dielectric which forms a capacitor plane. One conductor has a surface mount resistor to allow exact impedance matching to the core of a coaxial cable. The other conductor attaches electrically to the shield of the coaxial cable. The probe is stabilized in the brain tissue through a plastic ventriculostomy bolt which has been secured by screw tapping into the cranium. The coaxial cable connects to a spectrum analyzer. Brain water content and blood congestion alter the resonant frequency of the probe, allowing a realtime readout of apparent tissue water content. By monitoring the momentary shift in center resonant frequency or, alternatively, the standing wave ratio slightly off resonant frequency, a beat-to-beat pulsatile waveform is derived relating to the perfusion of the brain. A strain gauge intracranial pressure sensor (ICP) is separately affixed through the bolt and adjacent to the water content probe. By comparing the phase angle or lag time difference between the pressure tracing and the perfusion tracing, a realtime measurement of organ stiffness or compliance is derived.

17 Claims, 8 Drawing Sheets

WATER CONTENT PROBE

FIELD OF INVENTION

The invention relates to an apparatus and method for measuring local brain water content, perfusional pulsatile changes and the real time derivation of brain stiffness by comparison of perfusional and intracranial pressure tracings.

BACKGROUND OF INVENTION

Monitoring intracranial pressure (ICP) in real time in intensive care units has become an established standard of care in guiding physicians in the management of severe head injury. Treatment of head trauma increases pressure on the brain requiring monitoring intracranial pressure. This is particularly true in complicated cases of hydrocephalus as a post-craniotomy adjunct to detect brain swelling and in selected instances of brain infection and stroke. As brain swelling worsens due to the disease process, baseline pressure and waveform changes signal the need to aggressively attempt to reverse the course of the swelling with medications and pulmonary ventilation changes.

Intracranial pressure monitoring is normally performed by inserting a shunt through a hole in the cranium. A ventriculostomy catheter connected to an external pressure transducer is then introduced via the shunt into the brain substance. The shunt may also be used to drain excess fluid from the brain substance. An external pressure transducer provides accurate pressure measurements since a reliable baseline may be established. However, an external pressure transducer requires invasive procedures, risking a patient's health.

More recently, a miniaturized fiberoptic or strain gauge pressure transducer is inserted into the brain substance. The miniaturized transducer greatly reduces the invasiveness of the insertion procedure, but no practical method exists to establish a baseline measurement. This creates accuracy problems since many factors over the course of treatment may shift baseline measurements. Additionally, the ICP sensor and data from it alone do not allow a direct measurement of how edematous or congested the specific region of the brain is. Furthermore, swelling provides a widely ranging pressure change related to age and causes of the swelling. Finally, the ICP sensor alone does not provide a measurement of real time brain stiffness or compliance, a helpful indicator of imminent deterioration risk.

Static measurement may be achieved by magnetic resonance imaging ("MRI"), but this does not provide real time data. Real time information would greatly facilitate the detection of true shunt failure in the management of hydrocephalus. However, since real time measurement cannot be done with internal sensors, shunt failure must be inferred from late presenting clinical deterioration and anatomical changes as seen in imaging studies of the MRI. Additionally, the transport of a critically ill patient to an MRI facility is hazardous.

There is therefore a need for an instrument which may be inserted through a single aperture in the skull for simultaneous and continuous monitoring of both intracranial pressure and cerebral water content. There is another need for an instrument which may continuously measure pulsatile changes, altering apparent water content relating to beat-to-beat tissue perfusion due to cardiac output of blood to the brain. There is a further need for an instrument which provides the continuous measurement of tissue congestion related to venous back pressure from mechanical ventilation. There is another need for an instrument which derives the percent water content of the brain for comparison against normal values. There is yet another need for a system to monitor the more gradual baseline changes in wetness or brain edema of intracellular or extracellular origin related to the disease process. There is another need for an instrument which can simultaneously display the intracranial pressure (ICP) waveform and the pulsatile perfusional or momentary congestion changes of the brain. There is still another need for an apparatus and method for comparing the differences in lagtime between the ICP and perfusional waveforms, from which a realtime measurement of brain stiffness or compliance is derived.

SUMMARY OF THE INVENTION

These needs may be addressed by the present invention which is embodied in one aspect of the invention which is a probe for measuring tissue water content in a region of interest in the brain. The probe has an implantable tissue water content sensor having two plates with a proximal and distal end. The two plates are separated by a dielectric material and the distal end is implantable in brain tissue. An impedance matching circuit is coupled to the proximal end of one of the plates. A first output terminal is coupled to the matching circuit resistor and a second output terminal is coupled to one of the plates. A remotely positioned frequency spectrum analyzer receives an output signal from the first and second output terminals. A digital computer has a display, the digital computer having an input coupled to the output signal from the water content probe and the spectrum analyzer, the computer programmed to display the resonant frequency of the sensor indicative of water content in the brain tissue.

Another aspect of the present invention is a method of measuring tissue water content in a selected region of interest in the brain. A capacitive sensor having two plates outside the selected region of interest is calibrated and the resonant frequency of the sensor in air is determined. The capacitive sensor is calibrated in a mixture of water and NaCl. The resonant frequency of the sensor in the mixture is determined. A linear baseline frequency in relation to water content based on the resonant frequencies of the sensor in air and the mixture is established. The capacitive probe is implanted through a skull aperture such that the capacitive plates are exposed to the brain cortex and subjacent white matter. Interrogatory frequency scanning by a spectrum analyzer coupled to the sensor is produced to determine the center point of resonance by passage of the signal. True tissue water content is approximated by curve-fitting the frequency of resonance with the baseline frequency.

Another aspect of the present invention is a method of deriving beat-to-beat perfusional and congestion changes in brain tissue. The method includes inserting a water content probe having two conductive plates and a dielectric in the brain tissue. Signals at different frequencies on the water content probe are sent. A standing wave ratio at different frequencies is determined. A water content change tracing which fluctuates with cardiac output pulsatile perfusion of the tissue is then determined.

Another aspect of the present invention is a method of deriving realtime compliance or stiffness of brain tissue. The intracranial pressure of the brain tissue is measured. An intracranial waveform from the measurements of the intracranial pressure is then plotted. The pulsatile congestion changes in water content of the brain tissue is measured. A pulsatile congestion change waveform is plotted from the measurements of the pulsatile congestion change. The waveforms of intracranial pressure and the pulsatile congestion change in water content on a computer are simultaneously plotted. The stiffness of the brain is then determined from the simultaneous plotting.

Another aspect of the present invention is a probe for measuring tissue water content in a region of interest in the brain. The probe has an implantable tissue water content sensor having two plates with a proximal and distal end. The two plates are separated by a dielectric material and the distal end is implantable in brain tissue. A signal transmitting circuit is coupled to the proximal end of one of the plates. A signal receiver is provided. A remotely positioned frequency spectrum analyzer is coupled to the signal receiver. A digital computer is provided having a display and an input which is coupled to the output signal from the water content probe and the spectrum analyzer. The computer is programmed to display the resonant frequency of the sensor indicative of water content in the brain tissue.

It is to be understood that both the foregoing general description and the following detailed description are not limiting but are intended to provide further explanation of the invention claimed. The accompanying drawings, which are incorporated in and constitute part of this specification, are included to illustrate and provide a further understanding of the method and system of the invention. Together with the description, the drawings serve to explain the principles of the invention.

BRIEF DESCRIPTION OF DRAWINGS

This invention is pointed out with particularity in the appended claims. However, other objects and advantages together with the operation of the invention may be better understood by reference to the following illustrations, wherein:

DESCRIPTION OF THE PREFERRED EMBODIMENT

Figure 1:
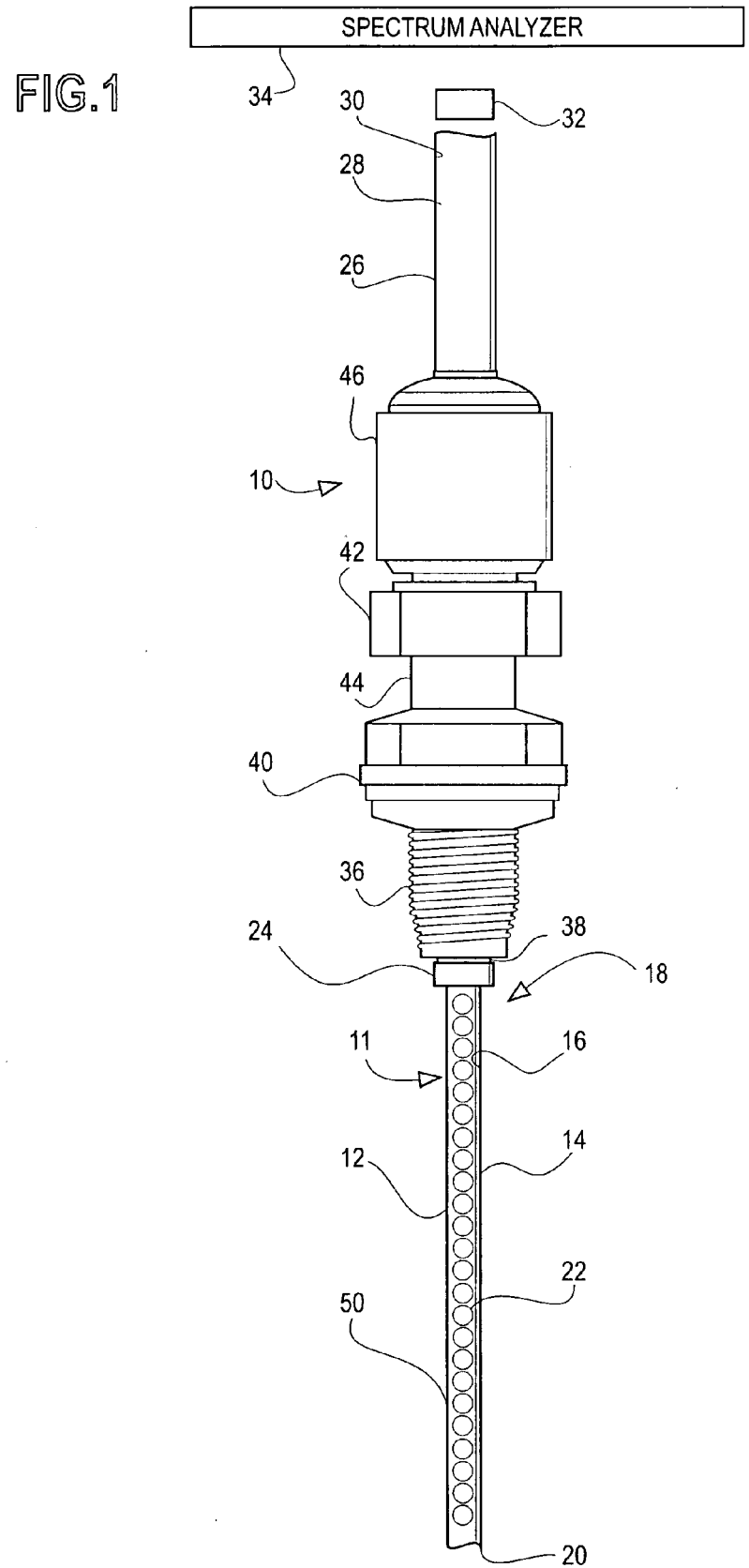
FIG. 1 is a perspective view of a brain stiffness probe according to an embodiment of the present invention.

While the present invention is capable of embodiment in various forms, there is shown in the drawings and will hereinafter be described a presently preferred embodiment with the understanding that the present disclosure is to be considered as an exemplification of the invention, and is not intended to limit the invention to the specific embodiment illustrated.

In accord with one embodiment of the invention, a combined probe 10 for measuring brain wetness and intracranial pressure is shown in FIG. 1. The probe 10 has a water content sensor 11 which has two conductive plates 12 and 14 on opposite sides of a printed circuit board (PCB) substrate 16. The conductive plates 12 and 14 are silver in the preferred embodiment but any suitable conductor material may be used. The substrate 16 in the preferred embodiment measures 5 cm in length, 2 mm in width, and 0.5 mm in depth. The probe 10 has a proximal end 18 and a distal end 20. Multiple holes 22 extend across the PCB substrate 16. The holes 22 increase sensitivity to real time pulsatile perfusional changes in tissue as they increase the surface area in contact with the brain tissue. The proximal end 18 has a surface mount resistor 24 on one side. A coaxial cable 26 has a core conductor member 28 and a shielding conductor 30 which is circumferentially located around the core member 28.

The surface mount resistor 24 is coupled between the proximal end 18 and one end of the coaxial cable 26. The surface mount resistor 24 provides impedance matching between the core 28 of the coaxial cable 26 and the plate 12. The impedance matching provided by the surface mount resistor 24 and the cable 26 is employed to achieve noise immunity in the cable 26 and allow the analysis electronics to be located at a distance from the water content sensor 11. Other types of impedance matching circuits such as a balanced antenna approach may be used as well. The plate 14 is connected directly to the shielding conductor 30 of the coaxial cable 26. The other end of the coaxial cable 26 is connected via an adapter 32 to a controller unit 34. In this sample, the adapter 32 is a PL250 type which minimizes signal loss to the cable 26.

The water content sensor 11 is inserted through a plastic bolt 36 via an aperture 38. The plastic bolt 36 has a pair of hex nuts 40 and 42 which are mounted on a main body section 44. The main body 44 has an exterior surface with threads. A lug nut 46 is coupled to the main body 44 and has corresponding interior threads. The lug nut 46 may be rotated on the main body 44 and provides a connection for the cable 26.

The probe 10 is inserted to a depth in brain tissue up to the plastic bolt 36 via the aperture. The hex nuts 40 and 42 and the lug nut 46 are tightened on the main body 44 of the bolt 36 to provide a seal and to allow the plastic bolt 36 to be positioned and held in the aperture 38. The bolt 36 is designed such that the surface mount resistor 24 lies about 1 mm above the surface of the brain, placing nearly the full length of the plates 12 and 14 in the brain tissue. Since the water of the brain bears a moderate salinity (typically 130–150 mEq Na+ per 1000 ml), an extremely thin-sputtered layer of insulation 50 insulates the electrical plates 12 and 14 from direct tissue contact. The insulation layer 50 is Teflon in the preferred embodiment, but any type of insulation may be used. The insulation layer 50 allows the point of resonance of the water content sensor 11 to be precisely measurable. The configuration of the capacitive plates 12 and 14 may be used in a tubular configuration to allow a silicone external ventricular drain through the lumen. In such a configuration, the electrically conductive plate surfaces are located on the length of the tube on opposite hemispheres to create a similar capacitive effect.

Figure 2:
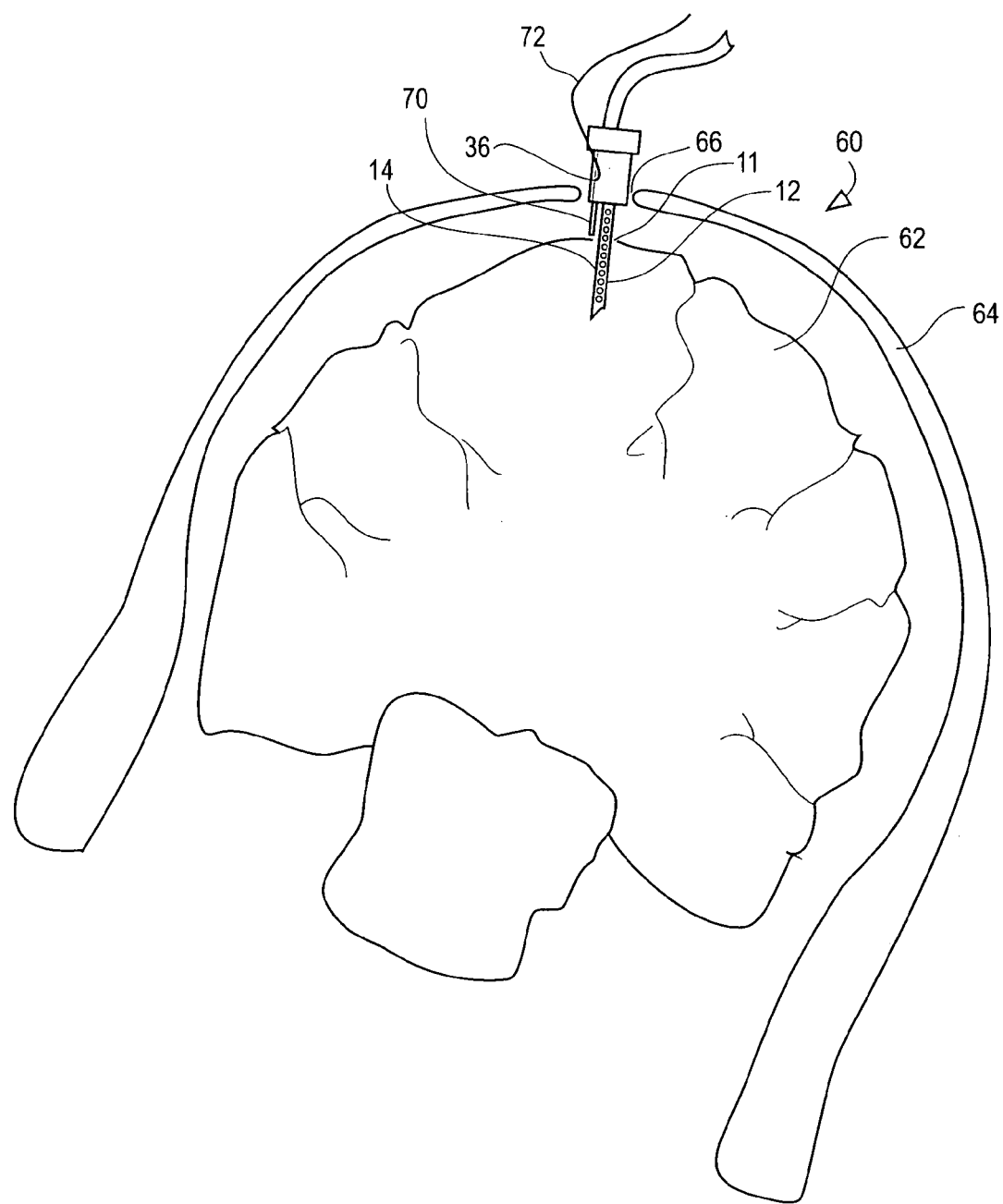
FIG. 2 is a partial cutaway view depicting the probe in FIG. 1 inserted through an aperture in the skull such that it is exposed to direct contact with brain tissue.

FIG. 2 shows a cutaway view of a head 60 with a brain 62 shown through the frontal lobes as seen by a typical MRI.

The brain 62 is encased by a cranium 64. The containment of the cranium 64 creates pressure on the brain 62 which may be excessive due to fluid buildup. A skull aperture 66 (or burr hole) is created in the cranium 64 after a scalp incision. This routine procedure in the intensive care unit would normally be followed by the introduction of an ICP sensor or ventriculostomy catheter as is presently known.

The plastic ventriculostomy bolt 36 in the preferred embodiment is commercially available through Codman and Shurtleff Incorporated, Raynham, Mass. The plastic bolt 36 is tapped and threaded snugly into the cranium 64. The water content sensor 11 is passed through the bolt 36 to a depth such that the sensing capacitive plates 12 and 14 are exposed to cortex and white matter of the brain 62. The plastic bolt 36 provides stable fixation of electrical connections and prevents movement of the sensor 11 in the brain 62 by secure fixation at the skull aperture 66 (burr hole).

An intra cranial pressure ("ICP") sensor 70 passes through the bolt 36 into the subjacent cortical tissue of the brain 62. The ICP sensor 70 is an electrical strain gauge type and measures changes in resistance due to pressure. Alternatively, any implantable pressure sensor such as a fiber optic sensor may be used. A fiber optic sensor has lasers coupled to dual fiber optic cables. A diaphragm is coupled to the end of the fiber optic cables and distorts light in reaction to pressure, producing changes in either light amplitude or frequency. In other cases, an external strain gauge which is coupled via tubing to a ventriculostomy catheter or a cranial bolt may be used to measure pressure.

The output voltage of the ICP sensor 70 is carried by a cable 72. The strain gauge ICP sensor 70 in this example is commercially available from Codman and Shurtleff Incorporated, Raynham, Mass. but any appropriate pressure sensor may be used. The ICP sensor 70 may be inserted separately from the bolt 36 and/or inserted at a separate site on the cranium if desired. This is to be avoided in most cases, but certain circumstances may require the separate insertion of the ICP sensor 70 and the water content sensor 11.

The respective wiring connections to and from the water content sensor 11 and the ICP sensor 70 are coupled to the controller unit 34 which is at a remote location. Alternatively, the cables may be connected to a signal transmitter if it is desired to eliminate the cables. The technique of positioning the combined sensors is identical to the routine insertion of a ventriculostomy catheter for monitoring and carries with it the same acceptably low risks.

Figure 3:
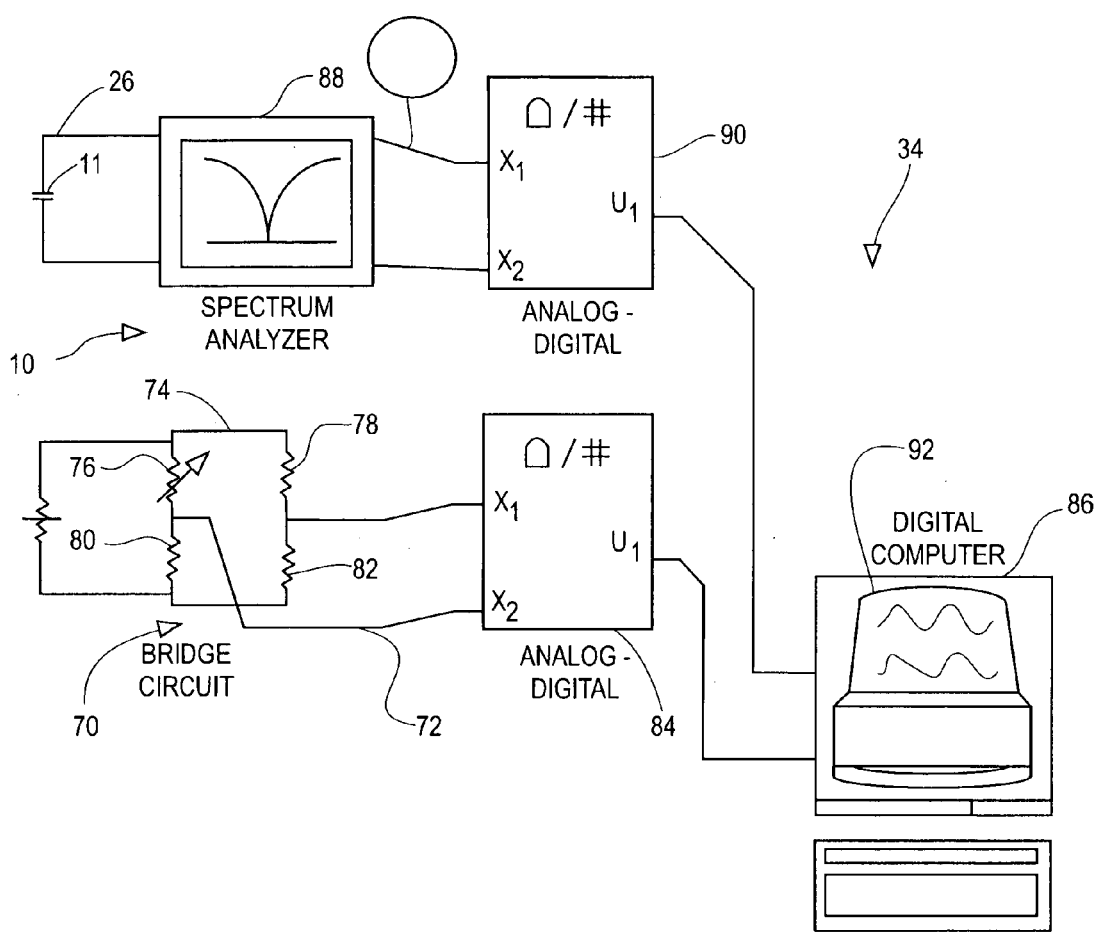
FIG. 3 is a block diagram with the probe components and remotely placed measuring equipment for both the water content sensor component and intracranial pressure component according to one embodiment of the present invention.

FIG. 3 is a block diagram of the control unit 34 of the combined ICP-water content probe 10. The ICP sensor 70 is a strain-gauge type which has a wheatstone bridge 74 of standard configuration having a pressure transducer 76 and three resistors 78, 80 and 82. The voltage of the bridge 74 changes in accordance to pressure changes on the pressure transducer 76. The output voltage of the bridge 74 represents the sensed pressure on transducer 76 and is coupled to the input of an analog to digital convertor 84 via the cable 72. The output of the analog to digital convertor 84 is coupled to a digital computer 86.

The water content sensor 11 is coupled via the coaxial cable 26 to an input of a spectrum analyzer 88. The spectrum analyzer 88 in the preferred embodiment is an AEA-Tempo 150-525 Analyst manufactured by Tempo Research of Vista, Calif. The spectrum analyzer 88 sweeps an interrogating frequency from 150 MHZ to 550 MHZ every 2 seconds to the water content sensor 11 in the preferred embodiment. The frequency spectrum for measuring brain water content without interference from other sources is optimally measured between 400 and 600 MHZ. However, other ranges may be useful depending on the probe length.

The direct output from the spectrum analyzer 88 is coupled to the digital computer 86 and a second output is coupled to an analog to digital convertor 90. This allows display of the resonant frequency of the water content sensor 11 determined from the direct output, as well as heart beat to heart beat changes in frequency and standing wave ratio (SWR) from the digital to analog converter 90. The outputs from the spectrum analyzer 88 and the digital to analog convertor 90 are plotted on a display 92. The display 92 is preferably a high resolution monitor but any display device may be used.

The digital computer 86 contains software necessary to simultaneously display the pulsatile waveform outputs from the ICP sensor 70 and the water content probe 11 on the display 92. As will be explained below, the brain water content and blood congestion alter the resonant frequency of the water content probe 11 and provides an indication of the real time read out of apparent tissue water content and the stiffness of the brain 62 which is independent of baseline water content or pressure.

FIGS. 4A–4D illustrates the process of probe calibration and water content determination of brain tissue which is displayed using the software on the digital computer 86 in conjunction with the display 92. The water content sensed by the water content sensor 11 of the probe 10 in FIGS. 1 and 2 is indicative of the effect of the surrounding tissue dielectric on the speed of transmission of the interrogating signal through the plates 12 and 14. Similar in concept to time domain reflectometry and familiar to those skilled in the art, the spectrum analyzer 88 will display a resonant frequency when the water content sensor 11 is placed in tissue. This resonance is a function of plate capacitance of the plates 12 and 14 (most strongly affected by probe length in this configuration) and the adjacent dielectric of the material of the substrate 16. The PCB dielectric material 16 between the plates 12 and 14 and the extremely thin-sputtered layer 50 have dielectric constants near air (dielectric of 1). In contrast, the brain is normally about 70% water. As the dielectric of H2O is 80, the tissue water content overwhelmingly determines the resonant frequency measured from the water content sensor 11.

Figure 4A:
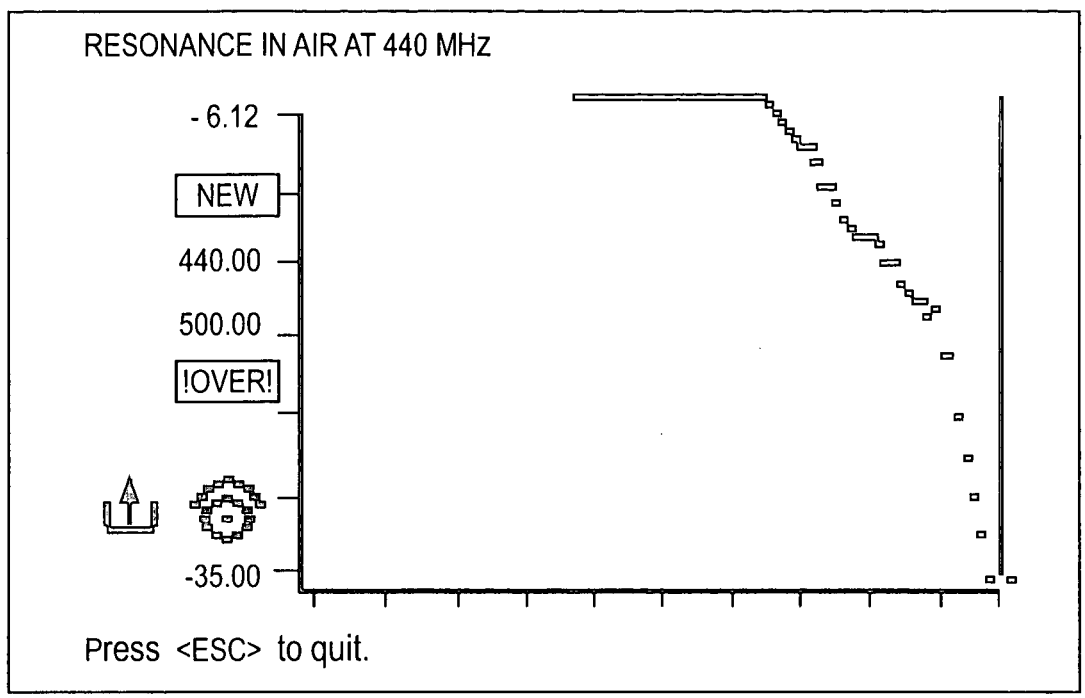
FIG. 4A–FIG. 4D are frequency resonance curves and calibration and measurement of tissue water content taken using a system according to the present invention.
Figure 4B:
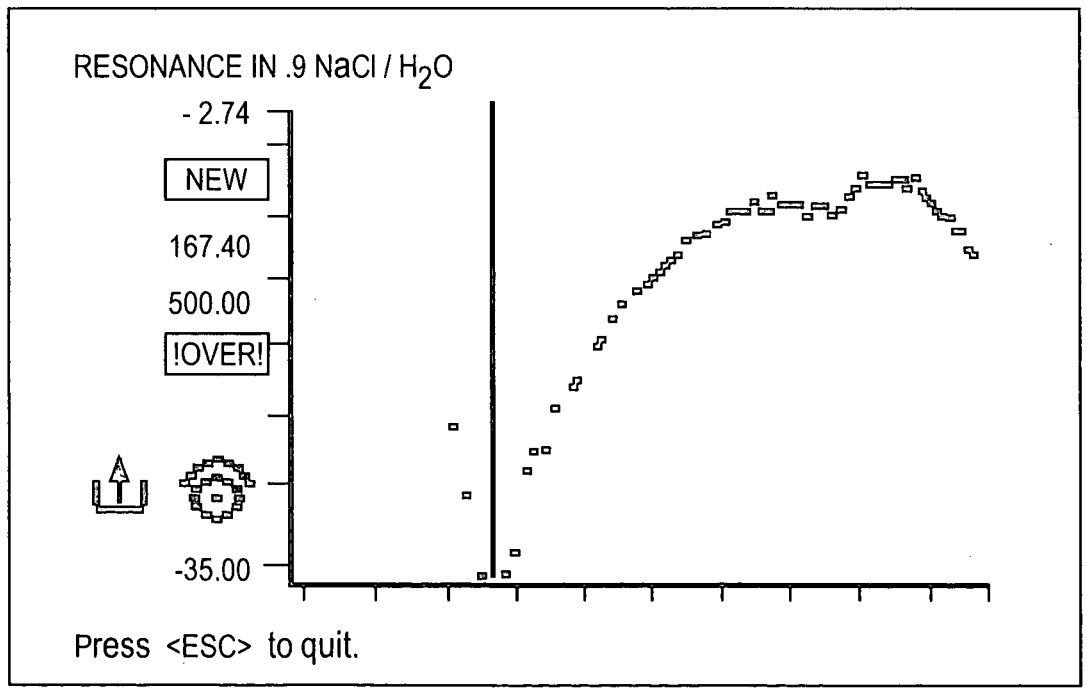

FIG. 4A shows the output plot of the spectrum analyzer 88 displayed by the digital computer 86 when the water content sensor 11 is entirely exposed to air. Since no significant water content related dielectric slows the signal in air, the resonant frequency of the water content sensor 11 is 440 MHZ. FIG. 4B shows the output plot when the water content sensor 11 is inserted in a 100% normal saline and water compound (simulating brain water and salinity). The resonant frequency of the water content sensor 11 has decreased to 167 MHZ as shown in FIG. 4B. This reduction is due to the overwhelming dielectric effect of the surrounding water with its high dielectric constant.

Figure 4C:
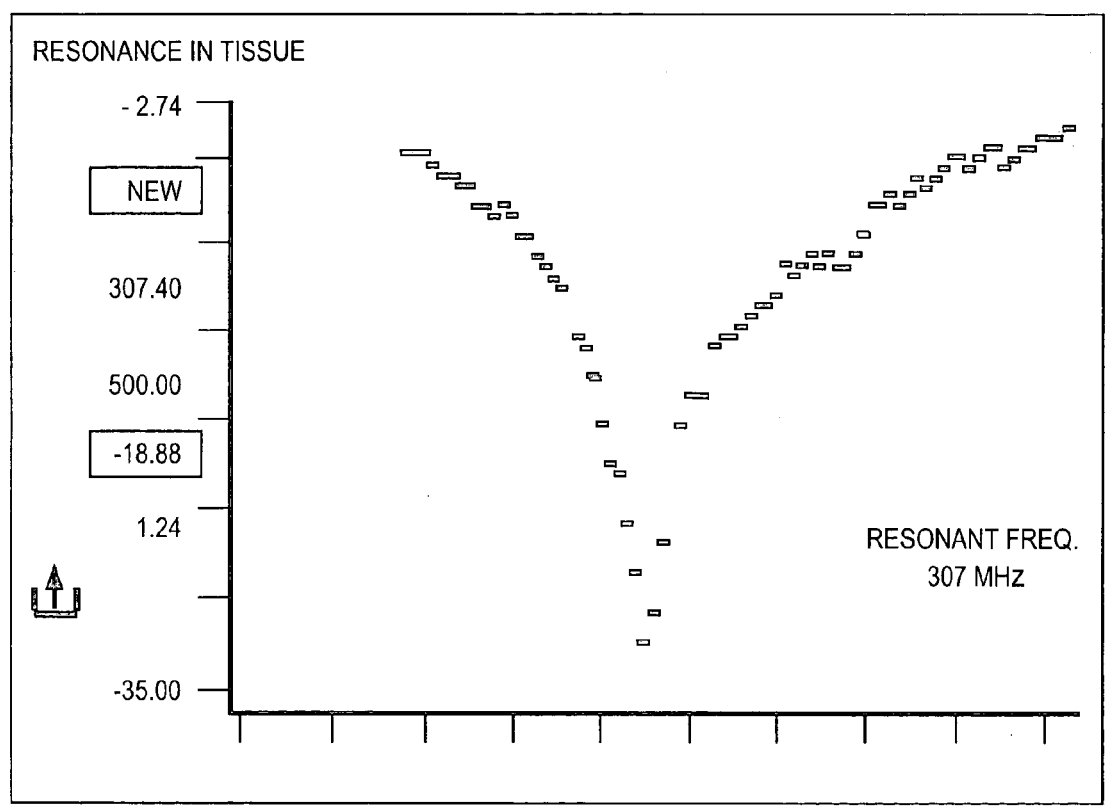
Figure 4D:
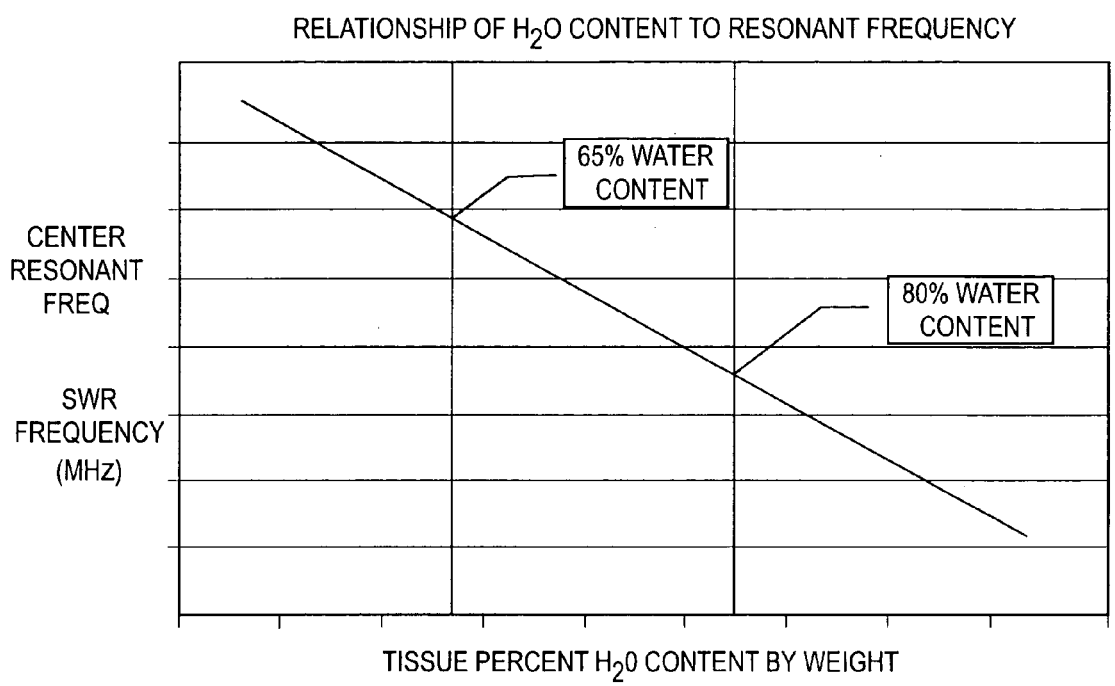

FIG. 4C shows the sharp resonant curve of the output of the water content sensor 11 when placed in the brain tissue 62 as shown in FIG. 2. The resonant frequency is 307 MHZ in FIG. 4C. The water content of the brain tissue 62 is proportional to the resonant frequency. The different resonant frequencies sensed by the sensor 11 in differing conditions of water content may be plotted. FIG. 4D shows the linearity of a typical output curve from the water content sensor 11 from submersing the sensor 11 in water as in FIG. 4A to full exposure in air as in FIG. 4B. By testing the water content sensor 11 in tissue utilizing dry and wet weight water content determinations, the linear range of clinical significance from 65% (very dehydrated brain) to 80% (very edematous brain) may be tested and provides a measurement standard for water content determination.

The measurable accuracy of the water content sensor 11 is up to 0.1% of water content change. In clinical use, however, the absolute local water content determination is not as useful as the trending of water content of the brain tissue over the course in the intensive care unit against a baseline measurement. The long term trends are more useful data since insertion of the water content sensor 11, as any probe, into the brain 62, causes a temporary injury edema which develops about the sensor 11 and artificially increases the baseline water content in the region. Additionally, effects of local minor accumulation of a non-flowing blood clot against the sensor plates 12 and 14 or incomplete passage to full depth of the plates 12 and 14 will offset the true water content baseline. Despite these considerations, the baseline measurement is used as a control against the course of illness and therapeutic intervention with dehydrating drugs such as furosemide and mannitol or ventilator changes provide a real time feedback of impact of the physician's regimen on the patient.

When the baseline water content is plotted over hours of time on a computer such as the computer 86, gradual shifts in the water content may be analyzed. For example, the initial shift in water content represents the initial placement edema and its resolution. The longer term shift in water content may represent the trend of brain swelling in the region of monitoring, edema due to head injury, or the effects of therapy. Alternatively, the changes in resonant frequency may also be logged using a spectrum/frequency 2 analyzer such as a Model HP8568A manufactured by Hewlett-Packard. However, much smaller changes of significance to the course of the illness may be measured from heart 4 beat to heart beat as will be explained below. Thus, the water content sensor 11 may be used in isolation without the associated intracranial pressure sensor 70, yielding profitable 6 data for the patient.

Figure 5:
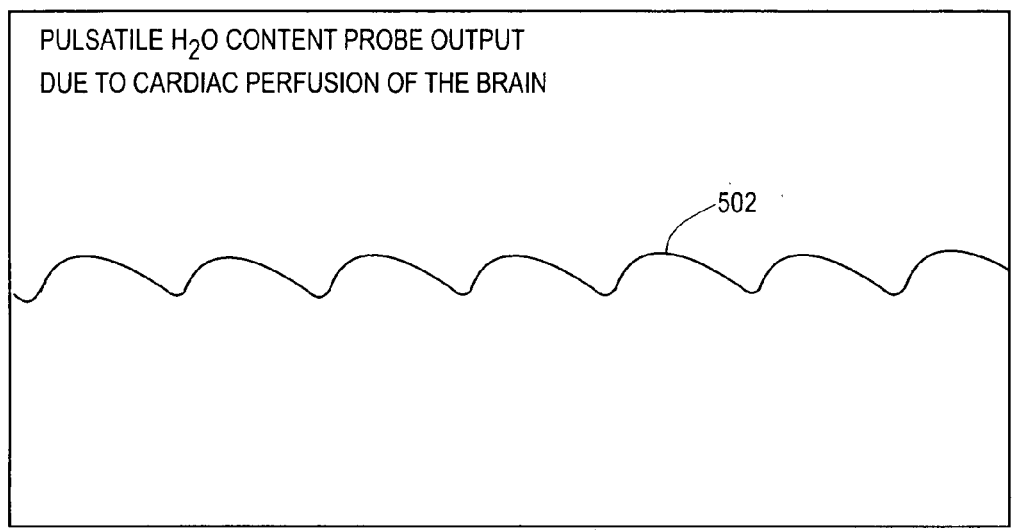
FIG. 5 is a waveform diagram showing pulsatile changes in microscopic center frequency shifts in the water content probe according to the present invention due to perfusion of the brain by cardiac pulsatile output.

FIG. 5 shows a pulsatile baseline 500 obtained from minute apparent water 8 content change. Either one of two techniques may be used to obtain the water content change on a heart beat to heart beat basis. The first technique involves use of the frequencies around the resonant frequency. When the spectrum analyzer 88 is employed to identify the standing wave ratio ("SWR") at resonance, a properly placed water content sensor 11 will show an SWR of 1.0. The frequency of resonance relates to the water content which is 307 MHZ in FIG. 4D.

However, if the frequency just to the right of the resonant point in FIG. 4D is selected where maximum change in SWR occurs per unit frequency change, typically an SWR of about 1.15, the beat-to-beat change of SWR may be plotted. The beat to beat SWR changes thus correlates to the local increased water content sensed by the water 18 content sensor 11 which is due to transient increased tissue congestion and arteriolar dilation due to blood flow. An undulating waveform 502 as a function of time is shown in FIG. 5. The undulating waveform 502 is measured from the water content sensor 11 as a function of the change in SWR from heart beat to heart beat. A slower baseline undulation relates to back pressure on the venous side of the brain from positive pressure ventilation of the patient or may be evoked by transient jugular vein compression (termed the Queckenstedt maneuver).

Figure 6:
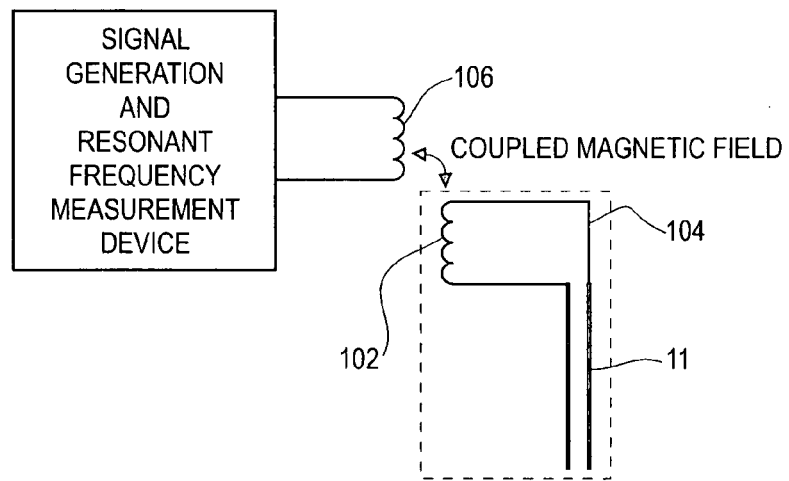
FIG. 6 is a block diagram of a wireless implementation of a water content probe according to the present invention.

Alternatively, the beat-to-beat effect may be measured by tracking the center frequency of resonance deviation when the water content sensor 11 in FIGS. 1 and 2 is viewed as the variable component of a simple LC resonant circuit 100 as shown in FIG. 6. The sensor 11 is coupled to an inductor 102. The sensor 11 and the inductor 102 may thus be integrated in an implanted sensor unit 104. A second inductor 106 is coupled to the processing circuitry which includes a signal generator and resonant frequency measurement device as explained above. Since the value of the first inductor 102 is fixed, the resonant frequency will shift as a function of water content of the tissue surrounding the sensor unit 104. The resonant frequency is measured wirelessly by sensing magnetic field energy from the second inductor 106 and the signal generator.

A significant advantage of this approach is that beat-to-beat pulsatile changes and baseline water content may be measured wirelessly using a spectrum analyzer pick-up circuit across the scalp from a wholly implanted resonant circuit. This technique allows long term, wireless monitoring of a region of interest over months to years for determining optimal compliance and control of hydrocephalus in patients treated by a ventriculoperitoneal shunting procedure.

Figure 7A:
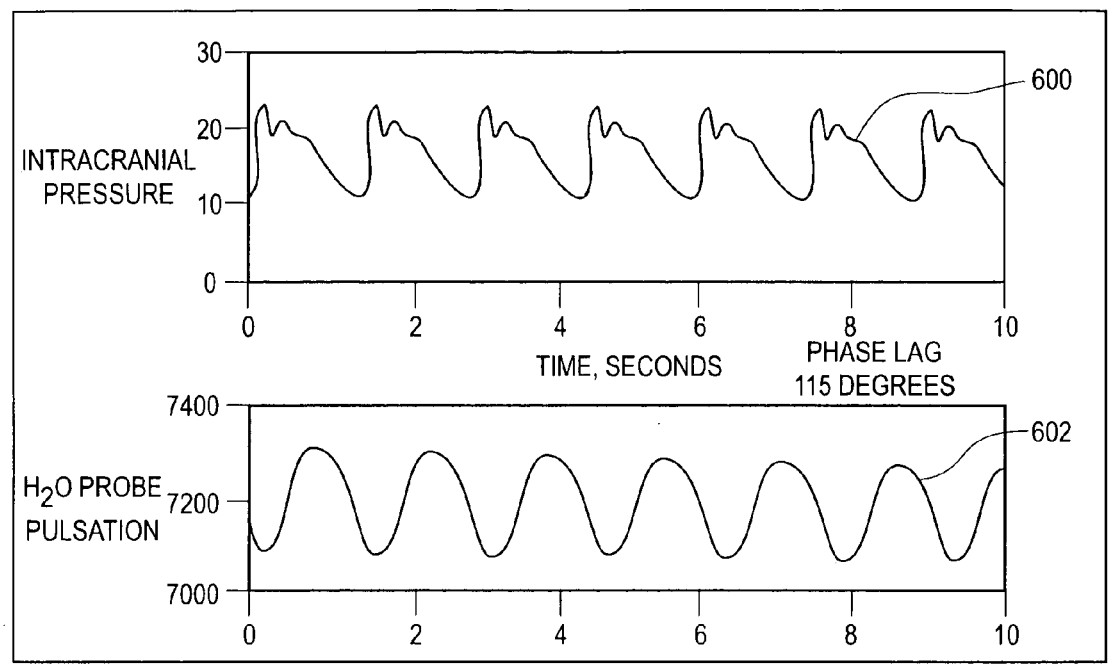
FIGS. 7A–7B are waveform diagrams which show the phase or lagtime relationship between the pressure waveform and perfusional waveform derived from the water content component of the combined probe according to the present invention.

With reference to FIGS. 1 and 2, when the intracranial pressure (ICP) waveform is plotted simultaneously with the pulsatile water content waveform derived from the two techniques described above, a phase relationship between the waveforms is seen. FIG. 7A shows a simultaneous plot of pressure 600 versus a pulsatile water content plot 602. The pressure plot 600 precedes pulsatile congestion as sensed by the water content probe plot 602. This indicates that peak vascular congestion lags peak pressure. FIG. 7A depicts the phase relationship plotted of a healthy, normal brain. In FIG. 7A, brain stiffness is within acceptable levels and thus the phase of beat to beat water content resonant frequency is phase shifted from the pressure changes by 115 degrees.

Figure 7B:
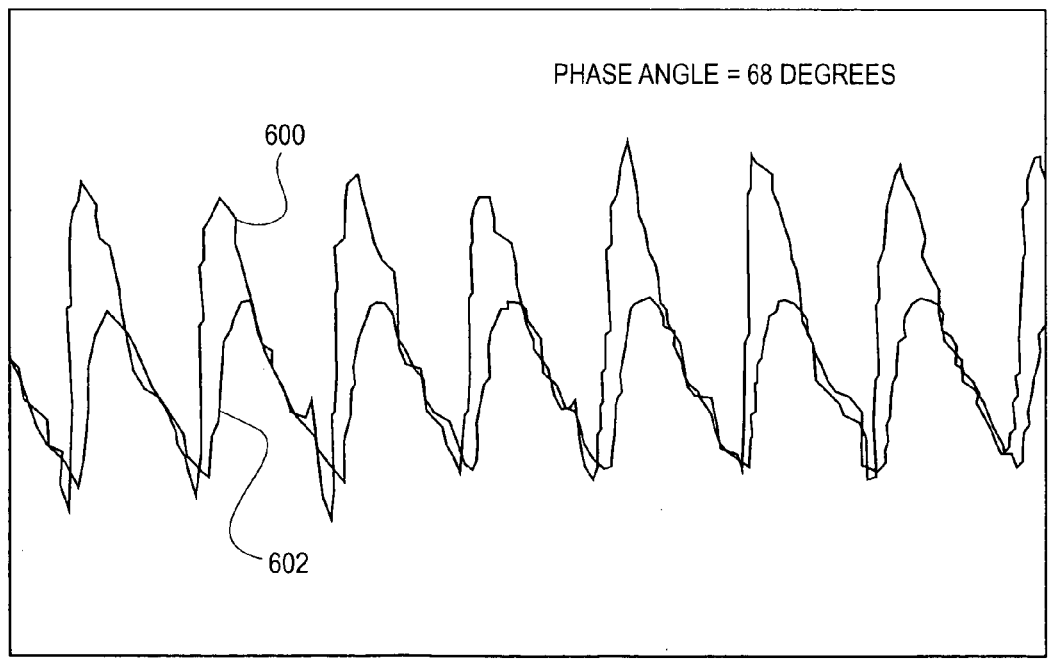

In contrast, FIG. 7B shows the pressure and water content plots 600 and 602 superimposed on each other in an example of worsening brain compliance or stiffness. The beat to beat water content resonant frequency is phase shifted from the pressure changes by 68 degrees. This relationship is also demonstrated by a combined ICP-blood flow probe such as when monitoring a patient with a thermal probe as described in U.S. Pat. No. 4,739,771 to the same inventors and incorporated by reference herein. In a normal, relaxed brain, the peak flow or vascular congestion may lag substantially, especially in a child with an open antereor fontanel. As the brain becomes progressively swollen with brain edema in head injury the lag narrows until the two waveforms are essentially co-incidental. Similarly, poor compliance in a patient with shunt failure will show the pattern of narrowing of lag time. The relationship can also be measured in real time as a function of phase lag adjusted for frequency (heart beat), akin to phase lag plotting in current phase compared to voltage phase in inductive circuits. Thus, the relationship by lag in seconds or phase angle adjusted for frequency provides a measure of brain stiffness which is independent of transducer amplitude, accuracy or stability, allowing a frequency domain relationship applicable to long term monitoring including implants.

It will be apparent to those skilled in the art that the disclosed measurement method and apparatus described above may be modified in numerous ways and assume many embodiments other than the preferred forms specifically set out and described above. Alternatives to the capacitive water content sensing technology include time domain reflectometry and square-wave frequency based sensors as well as fiberoptic sensors. The time domain reflectometry views the sensing components as a model transmission line. The reflection of a signal is measured as a function of water content. The square wave frequency based sensor uses a broad range of frequencies to determine water content as a function of the frequencies observed. The proper interpretation of the square wave frequency signals requires the appropriate circuitry. The fiberoptic sensor uses a light signal of a certain wavelength which is propagated down an implanted fiber. An optical grating is used to determine reflection of the light signal which is a function of the water content.

The pulsatile flow relationship to the ICP waveform can be derived by use of transducers such as thermistors (as described in the author's cited patent), or other heat clearance transducers as well as by transcranial impedance measurement and local tissue laser Doppler technique. The transcranial impedance measurement is performed by placing an ohmmeter on the head and measuring the signals at high frequency. An alternate impedance measurement may be used using a four probe method. Two impedance probes measure the output while two probes input the signal. The laser Doppler technique uses a laser to send a signal to the tissue of interest. The shift in Doppler frequency is measured to determine the water content.

An antenna sensor may be used for the water content sensor instead of the capacitive approach explained above. The entirety of the circuitry which includes the implanted circuit with an antenna to sense the water content in the tissue and a transmitter can be reduced to an integrated circuit as part of an implant or integrated onto the probe itself, allowing transcranial, wireless interrogation. The present invention is not limited by the foregoing descriptions but is intended to cover all modifications and variations that come within the scope of the spirit of the invention and the claims that follow.

What is claimed is:

1. A probe for measuring tissue water content in a region of interest in the brain, the probe comprising:
   an implantable tissue water content sensor having two plates with a proximal and distal end, the two plates being separated by a dielectric material and the distal end being implantable in brain tissue;
   an impedance matching circuit coupled to the proximal end of one of the plates;
   a first output terminal coupled to the matching circuit and a second output terminal coupled to one of the plates;
   a remotely positioned frequency spectrum analyzer receiving an output signal from the first and second output terminals; and
   a digital computer having a display, the digital computer having an input coupled to the output signal from the water content probe and the spectrum analyzer, the computer programmed to display the resonant frequency of the sensor indicative of water content in the brain tissue.

2. The probe of claim 1 wherein the two plates are coated with insulation material sufficient to provide DC isolation.

3. The probe of claim 1 wherein the impedance matching circuit includes a resistor.

4. The probe of claim 1 further comprising a coaxial cable having a core conductor coupled to the impedance matching circuit and a circumferential conductor coupled to the proximal end of the other plate, the coaxial cable being coupled to the spectrum analyzer.

5. The probe of claim 1 wherein the plates and the dielectric material have a series of transverse holes.

6. The probe of claim 1 further comprising an intracranial pressure sensor located in substantially parallel orientation with the water content sensor and reading the pressure of the region of interest.

7. The probe of claim 6 further comprising:
   an analog to digital converter having an output and an input coupled to the intracranial pressure sensor; and
   wherein the computer is coupled to the output of the analog to digital converter and is programmed to display simultaneous tracings of apparent water content pulsatility due to tissue perfusion and compression based on the signal from the spectrum analyzer and the intracranial pressure waveform.

8. The probe of claim 7 wherein the pressure sensor is a tissue-implanted strain gauge.

9. The probe of claim 7 wherein the pressure sensor is a fiberoptic sensor.

10. The probe of claim 7 further comprising:
    a wireless transmitter coupled to the intracranial sensor and the water content sensor; and
    a wireless receiver coupled to the digital computer, the receiver tuned to signals from the transmitter.

11. The probe of claim 10 wherein the impedance matching and transmitter circuit components are an implantable component integrated circuit of the sensor probe.

12. The probe of claim 7 wherein the digital computer determines apparent water content pulsatility due to tissue perfusion and compression by plotting the change in standing wave ratio to the side of the return loss curve on the spectrum analyzer and determines where the standing wave ratio change is at a maximum.

13. The probe of claim 7 further comprising an inductor coupled in parallel to the plates of the water content probe, and wherein the digital computer determines apparent water content pulsatility due to tissue perfusion and compression by plotting the center frequency resonance shift.

14. The probe of claim 6 further comprising a threaded, self-tapping bolt insertable within a skull aperture, the bolt having a first opening which allows stabilization and positioning of the water content sensor and a second opening which allows stabilization and position of the intracranial pressure sensor.

15. The probe of claim 1 wherein the plates are coupled to a shunt tube which serves as a ventrical drain from the region of interest.

16. A probe for measuring tissue water content in a region of interest in the brain, the probe comprising:
    an implantable tissue water content sensor having two plates with a proximal and distal end, the two plates being separated by a dielectric material and the distal end being implantable in brain tissue;
    a signal transmitting circuit coupled to the proximal end of one of the plates;
    a signal receiver;
    a remotely positioned frequency spectrum analyzer coupled to the signal receiver; and
    a digital computer having a display, the digital computer having an input coupled to the output signal from the water content probe and the spectrum analyzer, the computer programmed to display the resonant frequency of the sensor indicative of water content in the brain tissue.

17. The probe of claim 16 wherein the transmitter circuit includes an inductor and the signal receiver includes a second inductor wherein magnetic field energy is applied to the second inductor.

* * * * *